United States Patent
Sato et al.

(10) Patent No.: US 6,329,539 B1
(45) Date of Patent: Dec. 11, 2001

(54) PROSTAGLADIN DERIVATIVES

(75) Inventors: Fumie Sato, 2-1-901, Kugenumahigashi, Fugisawa-shi, Kanagawa 251-0026 (JP); Tohru Tanami; Kazuya Kameo, both of Tokyo (JP); Kenji Yamada, Tokyo (JP); Shigeru Okuyama, Tokyo (JP); Naoya Ono, Tokyo (JP)

(73) Assignees: Taisho Pharmaceutical Co., Ltd., Tokyo; Fumie Sato, Kanagawa, both of (JP)

( * ) Notice: Subject to any disclaimer, the term of this patent is extended or adjusted under 35 U.S.C. 154(b) by 0 days.

(21) Appl. No.: 09/701,187
(22) PCT Filed: May 25, 1999
(86) PCT No.: PCT/JP99/02721
§ 371 Date: Nov. 27, 2000
§ 102(e) Date: Nov. 27, 2000
(87) PCT Pub. No.: WO99/61419
PCT Pub. Date: Dec. 2, 1999

(30) Foreign Application Priority Data

May 25, 1998 (JP) .................................. 10-142622

(51) Int. Cl.$^7$ .................................................. C07C 59/00
(52) U.S. Cl. .................................... 554/214; 514/530
(58) Field of Search .............................. 554/214; 514/530

(56) References Cited

U.S. PATENT DOCUMENTS

| | | | |
|---|---|---|---|
| 5,073,569 | 12/1991 | Ueno et al. | 514/530 |
| 5,137,915 | 8/1992 | Ueno et al. | 514/530 |
| 5,534,547 | 7/1996 | Ueno | 514/530 |
| 5,639,899 | 6/1997 | Sato et al. | 554/117 |

FOREIGN PATENT DOCUMENTS

| | | | |
|---|---|---|---|
| 1-104040 | 4/1989 | (JP) | C07C/177/00 |
| 5-117230 | 5/1993 | (JP) | C07C/405/00 |
| 6-277080 | 10/1994 | (JP) | C12P/7/42 |

Primary Examiner—Deborah D. Carr
(74) Attorney, Agent, or Firm—Sughrue, Mion, Zinn, Macpeak & Seas, PLLC

(57) ABSTRACT

A prostaglandin derivative represented by the formula:

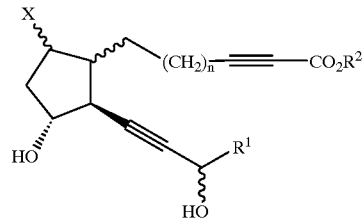

wherein X is a halogen atom, n is an integer of 1 to 5, $R^1$ is a $C_{3-10}$ cycloalkyl group, a $C_{3-10}$ cycloalkyl group substituted with $C_{1-4}$ alkyl group(s), a $C_{4-13}$ cycloalkylalkyl group, a $C_{5-10}$ alkyl group, a $C_{5-10}$ alkenyl group, a $C_{5-10}$ alkynyl group or a bridged cyclic hydrocarbon group, and $R^2$ is a hydrogen atom, a $C_{1-10}$ alkyl group or a $C_{3-10}$ cycloalkyl group, or a pharmaceutically acceptable salt thereof.

6 Claims, No Drawings

PROSTAGLADIN DERIVATIVES

This application is a 371 of PCT/JP99/02721 filed May 25, 1999.

TECHNICAL FIELD

The present invention relates to novel prostaglandin derivatives.

BACKGROUND ART

Since prostaglandin (hereinafter referred to as "PG") exhibits various important physiological actions in a trace amount, the syntheses of the derivatives from natural PGs and the biological activities have been investigated with the intention of a practical use as medicines and have been reported in many literatures.

Particularly, PGs have been reported on their various central nervous actions and have been clarified as to the intracerebral content, biosynthesis, metabolic pathway, their intracerebral localizations and changes with growth or aging, and there has been taken an interest in the relation of PGs with sleep and wake. Among them, $PGD_2$ has been known as an intracerebral humoral factor which controls the occurrence or maintenance of sleep, and it was made clear that the sleep induced by $PGD_2$ in monkeys is undistinguished from the spontaneous natural sleep in brain wave or behavior (Proc. Natl. Acad. Sci. USA, vol. 85, pp. 4082–4086 (1988)), therefore this compound was expected as a compound having a novel sleep-inducing action.

However, $PGD_2$ derivatives including $PGD_2$ are presently unpractical due to the problems concerning the effect and the stability as a drug.

DISCLOSURE OF THE INVENTION

As a result of the extensive studies, the present inventors have found that the prostaglandin derivatives having a triple bond between the 13- and 14-positions represented by the following Formula (I) have a characteristic sleep-inducing action, and thereby the present invention has been accomplished.

That is, the present invention is directed to a prostaglandin derivative represented by Formula (I):

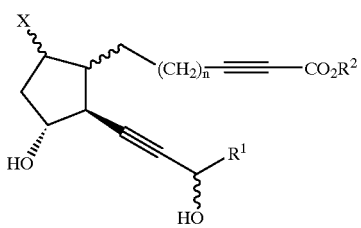

(I)

wherein X is a halogen atom, n is an integer of 1 to 5, $R^1$ is a $C_{3-10}$ cycloalkyl group, a $C_{3-10}$ cycloalkyl group substituted with $C_{1-4}$ alkyl group(s), a $C_{4-13}$ cycloalkylalkyl group, a $C_{5-10}$ alkyl group, a $C_{5-10}$ alkenyl group, a $C_{5-10}$ alkynyl group or a bridged cyclic hydrocarbon group, and $R^2$ is a hydrogen atom, a $C_{1-10}$ alkyl group or a $C_{3-10}$ cycloalkyl group, or a pharmaceutically acceptable salt thereof.

Further, the present invention is directed to a prostaglandin derivative represented by Formula (I) wherein $R^1$ is a $C_{3-10}$ cycloalkyl group, a $C_{3-10}$ cycloalkyl group substituted with $C_{1-4}$ alkyl group(s) or a $C_{4-13}$ cycloalkylalkyl group, and X, n and $R^2$ are as defined above, or a pharmaceutically acceptable salt thereof.

Furthermore, the present invention is directed to a pharmaceutical composition which comprises as an effective ingredient the above-mentioned prostaglandin derivative represented by Formula (I) or the pharmaceutically acceptable salt thereof.

Still furthermore, the present invention is directed to a sleep-inducing preparation which comprises as an effective ingredient the above-mentioned prostaglandin derivative represented by Formula (I) or the pharmaceutically acceptable salt thereof.

Still furthermore, the present invention is directed to a method for sleep-inducing comprising administering a pharmacologically effective amount of the above-mentioned prostaglandin derivative or the pharmaceutically acceptable salt to a human.

In the present invention, the halogen atom refers to a fluorine atom, a chlorine atom, a bromine atom or an iodine atom.

Examples of the $C_{3-10}$ cycloalkyl group are a cyclopropyl group, a cyclobutyl group, a cyclopentyl group, a cyclohexyl group and a cycloheptyl group.

Examples of the $C_{3-10}$ cycloalkyl group substituted with $C_{1-4}$ alkyl group(s) are a methylcyclopropyl group, a methylcyclohexyl group and an ethylcyclohexyl group.

Examples of the $C_{4-13}$ cycloalkylalkyl group are a cyclopropylmethyl group, a cyclobutylmethyl group, a cyclopentylmethyl group, a cyclopentylethyl group, a cyclohexylmethyl group, a cyclohexylethyl group and a cycloheptylmethyl group.

The $C_{5-10}$ alkyl group refers to a straight or branched alkyl group, and examples thereof are a pentyl group, a hexyl group, a heptyl group, an octyl group, a 1-methylpentyl group, a 2-methylpentyl group, a 1-methylhexyl group, a 2-methylhexyl group, a 2,4-dimethylpentyl group, a 2-ethylpentyl group, a 2-methylheptyl group, a 2-ethylhexyl group, a 2-propylpentyl group, a 2-propylhexyl group and a 2,6-dimethylheptyl group.

The $C_{5-10}$ alkenyl group refers to a straight or branched alkenyl group, and examples thereof are a 3-pentenyl group, a 4-hexenyl group, a 5-heptenyl group, a 4-methyl-3-pentenyl group, a 2,4-dimethylpentenyl group, a 6-methyl-5-heptenyl group and a 2,6-dimethyl-5-heptenyl group.

The $C_{5-10}$ alkynyl group refers to a straight or branched alkynyl group, and examples thereof are a 3-pentynyl group, a 3-hexynyl group, a 4-hexynyl group, a 1-methylpent-3-ynyl group, a 2-methylpent-3-ynyl group, a 1-methylhex-3-ynyl group and a 2-methylhex-3-ynyl group.

Examples of the bridged cyclic hydrocarbon group are a bornyl group, a norbornyl group, an adamantyl group, a pinanyl group, a thujyl group, caryl group and a camphanyl group.

The $C_{1-10}$ alkyl group for $R^2$ refers to a straight or branched alkyl group, and examples thereof are a methyl group, an ethyl group, a propyl group, an isopropyl group, a butyl group, an isobutyl group, a tert-butyl group, a pentyl group, an isopentyl group, a 2-ethylpropyl group, a hexyl group, an isohexyl group, a 1-ethylbutyl group, a heptyl group, an isoheptyl group, an octyl group, a nonyl group and a decyl group.

Examples of the pharmaceutically acceptable salt are salts with alkali metal (e.g. sodium or potassium), alkali earth metal (e.g. calcium or magnesium), ammonia, methylamine, dimethylamine, cyclopentylamine, benzylamine, piperidine, monoethanolamine, diethanolamine, monomethylmonoethanolamine, tromethamine, lysine, a tetraalkyl ammonium and tris(hydroxymethyl)aminomethane.

The compounds of Formula (I) of the present invention can be prepared, for example, by the methods summarized by the following reaction formulae.

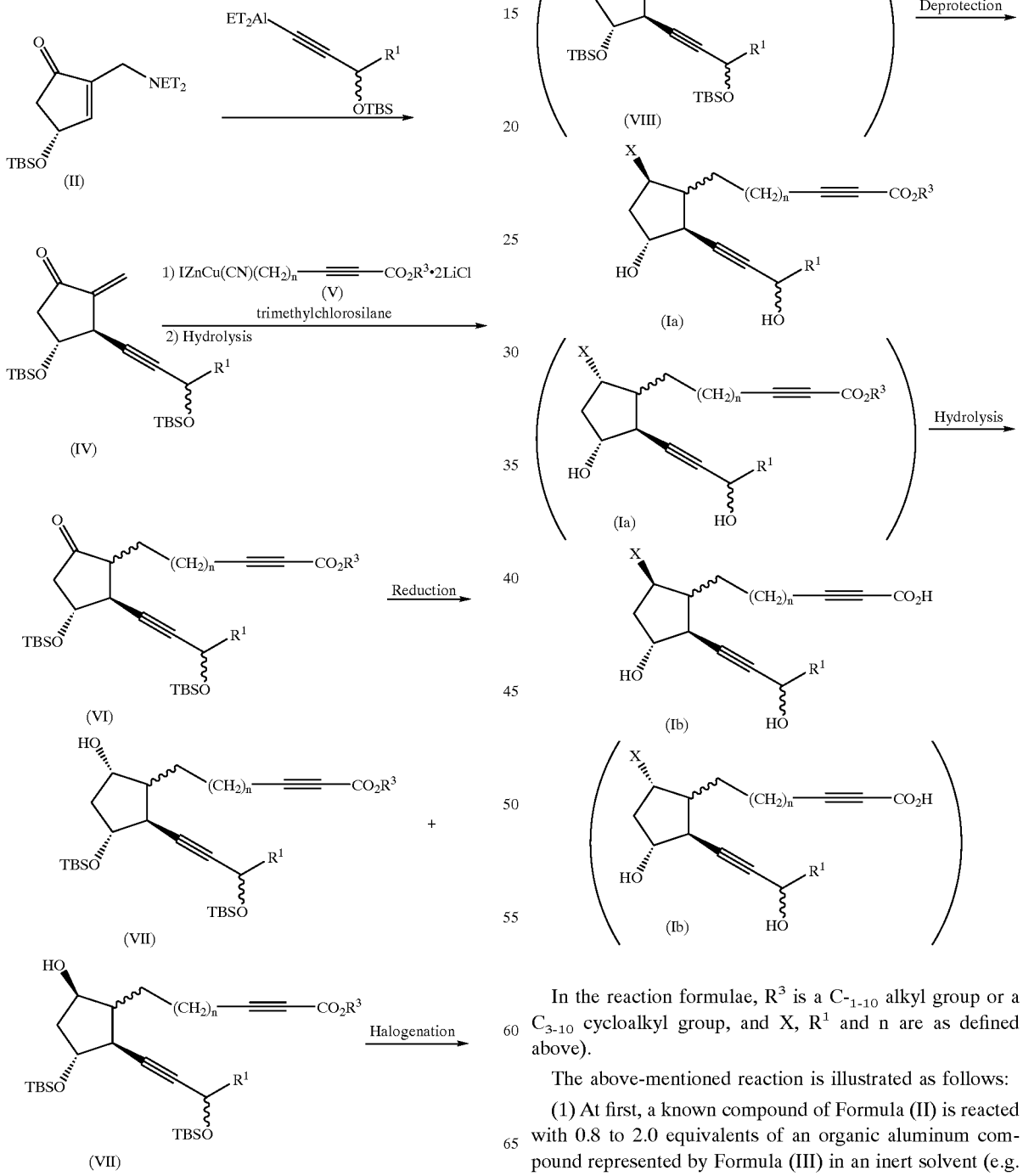

In the reaction formulae, $R^3$ is a $C_{1-10}$ alkyl group or a $C_{3-10}$ cycloalkyl group, and X, $R^1$ and n are as defined above).

The above-mentioned reaction is illustrated as follows:

(1) At first, a known compound of Formula (II) is reacted with 0.8 to 2.0 equivalents of an organic aluminum compound represented by Formula (III) in an inert solvent (e.g. benzene, toluene, tetrahydrofuran, diethyl ether, methylene chloride or n-hexane) at −10 to 30° C., preferably 0 to 10° C., according to the method of Sato et al. (Journal of Organic Chemistry, vol. 53, page 5590 (1988)) to stereospecifically give a compound of Formula (IV).

(2) The compound of Formula (IV) is reacted with 0.5 to 4.0 equivalents of an organic copper compound represented by Formula (V) and 0.5 to 4.0 equivalents of trimethylchlorosilane in an inert solvent (e.g. benzene, toluene, tetrahydrofuran, diethyl ether, methylene chloride, n-hexane or n-pentane) at −78 to 40° C., followed by hydrolysis using an inorganic acid (e.g. hydrochloric acid, sulfuric acid or nitric acid) or organic acid (e.g. acetic acid or p-toluenesulfonic acid) or an amine salt thereof (e.g. pyridinium p-toluenesulfonate) in an organic solvent (e.g. acetone, methanol, ethanol, isopropanol, diethyl ether or a mixture thereof) at 0 to 40° C. to stereoselectively give a compound of Formula (VI).

(3) The compound of Formula (VI) is reduced with 0.5 to 5 equivalents of a reductant (e.g. potassium borohydride, sodium borohydride, sodium cyanoborohydride or lithium tri-sec-butyl borohydride) in an organic solvent (e.g. tetrahydrofuran, diethyl ether, ethyl alcohol or methyl alcohol) at −78 to 40° C. to give compounds of Formulae (VII) and (VII'). These compounds of Formulae (VII) and (VII') can be purified by a conventional separation method such as column chromatography.

(4) The compound of Formula (VII) or (VII') is mesylated or tosylated, for example, with 1 to 6 equivalents of methanesulfonyl chloride or p-toluenesulfonyl chloride in a proper solvent such as pyridine (if necessary, in the presence of 0.8 to 6 equivalents of 4-dimethylaminopyridine) at −20 to 40° C., followed by chlorination with 1 to 16 equivalents of tetra-n-butylammonium chloride to give a compound of Formula (VIII) or (VIII') wherein X is a a chlorine atom, respectively.

Herein, bromination or fluorination can be also carried out in an ordinary manner. For example, bromination can be carried out by a reaction with 1 to 10 equivalents of carbon tetrabromide in the presence of 1 to 10 equivalents of triphenylphosphine and 1 to 10 equivalents of pyridine in acetonitrile, and fluorination can be carried out by a reaction with 5 to 20 equivalents of diethylaminosulfur trifluoride (DAST) in methylene chloride.

(5) The protective group of the hydroxyl group of the compound of Formula (VIII) or (VIII'), i.e. a tert-butyldimethylsilyl group is removed by using hydrofluoric acid, pyridinium poly(hydrogenfluoride) or hydrochloric acid under conventional conditions in a solvent (e.g. methanol, ethanol, acetonitrile, a mixture thereof or a mixture of these solvents and water) to give a PG derivative of Formula (Ia) or (Ia').

(6) The PG derivative of Formula (Ia) or (Ia') is hydrolyzed using 1 to 6 equivalents of a base in a solvent ordinarily used for hydrolysis to give a PG derivative of Formula (Ib) or (Ib') of the present invention. Examples of the base to be used herein are lithium hydroxide and potassium carbonate, and examples of the solvent are acetonitrile, acetone, methanol, ethanol, water and a mixture thereof.

Furthermore, the compound of Formula (Ia) or (Ia') is hydrolyzed by a reaction with an enzyme in. a buffer solution such as phosphate buffer or tris-hydrochloride buffer, if necessary, by using an organic solvent (e.g. a water-miscible solvent such as acetone, methanol or ethanol) to give the prostaglandin derivative of the present invention, i.e. the compound of Formula (Ib) or (Ib'). Examples of the enzyme to be used herein are enzymes produced by microorganisms (e.g. enzymes produced by microorganisms belonging to Candida sp. or Pseudomonas sp.) and enzymes prepared from animal organs (e.g. pig liver or pig pancreas). Commercially available enzymes are, for example, lipase VII (derived from microorganism of Candida sp.; Sigma Co.), lipase AY (derived from microorganism of Candida sp.; Amano Pharmaceutical Co.), lipase AY (derived from microorganism of Pseudomonas sp.; Amano Pharmaceutical Co.), lipase PS (derived from microorganism of Pseudomonas sp.; Amano Pharmaceutical Co.), lipase MF (derived from microorganism of Pseudomonas sp.; Amano Pharmaceutical Co.), PLE (prepared from pig liver; Sigma Co.), lipase II (prepared from pig pancreas; Sigma Co.) or lipoprotein lipase (prepared from pig pancreas; Tokyo Kasei Kogyo Co.).

The amount of the enzyme to be used, while depending on the potency of the enzyme and the amount of the substrate (the compound of Formula (Ia)), is usually 0.1 to 20 parts by weight based on the substrate, and the reaction temperature is from 25 to 50° C., preferably 30 to 40° C.

The compounds of Formula (I) of the present invention are, for example, as follows.

TABLE 1

(I)

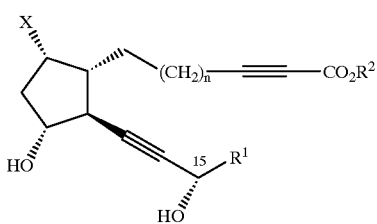

| Compound No. | X | n | $R^1$ | $R^2$ | 8-position | 15-position |
|---|---|---|---|---|---|---|
| Compound 1 | β-Cl | 1 | cyclopentyl | methyl | α | α |
| Compound 2 | β-Cl | 2 | cyclopentyl | methyl | α | α |
| Compound 3 | β-Cl | 2 | cyclopentyl | hydrogen | α | α |
| Compound 4 | β-Cl | 3 | cyclopentyl | methyl | α | α |
| Compound 5 | β-Cl | 3 | cyclopentyl | hydrogen | α | α |
| Compound 6 | β-Cl | 4 | cyclopentyl | methyl | α | α |
| Compound 7 | β-Cl | 4 | cyclopentyl | hydrogen | α | α |
| Compound 8 | β-Cl | 3 | cyclohexyl | tert-butyl | α | α |
| Compound 9 | β-Cl | 3 | cyclohexyl | methyl | β | α |
| Compound 10 | β-Cl | 3 | cyclohexyl | hydrogen | β | α |
| Compound 11 | β-Cl | 2 | cyclohexyl | methyl | α | α |
| Compound 12 | β-Cl | 2 | cyclohexyl | hydrogen | α | α |
| Compound 13 | β-Cl | 3 | cyclohexyl | methyl | α | α |
| Compound 14 | β-Cl | 3 | cyclohexyl | hydrogen | α | α |
| Compound 15 | β-Br | 3 | cyclohexyl | methyl | α | α |
| Compound 16 | β-Br | 3 | cyclohexyl | hydrogen | α | α |
| Compound 17 | F | 3 | cyclohexyl | methyl | α | α |
| Compound 18 | F | 3 | cyclohexyl | hydrogen | α | α |
| Compound 19 | β-Cl | 4 | cyclohexyl | methyl | α | α |
| Compound 20 | β-Cl | 4 | cyclohexyl | hydrogen | α | α |
| Compound 21 | β-Cl | 3 | cyclohexyl | methyl | α | β |
| Compound 22 | β-Cl | 3 | cyclohexyl | hydrogen | α | β |
| Compound 23 | β-Cl | 4 | cyclohexyl | methyl | α | β |
| Compound 24 | β-Cl | 4 | cyclohexyl | hydrogen | α | β |

TABLE 1-continued (I)

| Compound No. | X | n | $R^1$ | $R^2$ | 8-position | 15-position |
|---|---|---|---|---|---|---|
| Compound 25 | α-Cl | 3 | cyclohexyl | methyl | α | α |
| Compound 26 | α-Cl | 3 | cyclohexyl | hydrogen | α | α |
| Compound 27 | β-Cl | 3 | cycloheptyl | methyl | α | α |
| Compound 28 | β-Cl | 3 | cycloheptyl | hydrogen | α | α |
| Compound 29 | β-Cl | 2 | cyclopentyl-methyl | methyl | α | α |
| Compound 30 | β-Cl | 2 | cyclopentyl-methyl | hydrogen | α | α |
| Compound 31 | β-Cl | 3 | cyclopentyl-methyl | cyclohexyl | α | α |
| Compound 32 | β-Cl | 3 | cyclopentyl-methyl | methyl | α | α |
| Compound 33 | β-Cl | 3 | cyclopentyl-methyl | hydrogen | α | α |
| Compound 34 | β-Br | 3 | cyclopentyl-methyl | methyl | α | α |
| Compound 35 | β-Br | 3 | cyclopentyl-methyl | hydrogen | α | α |
| Compound 36 | β-Cl | 4 | cyclopentyl-methyl | methyl | α | α |
| Compound 37 | β-Cl | 4 | cyclopentyl-methyl | hydrogen | α | α |
| Compound 38 | β-Cl | 3 | cyclohexyl-methyl | methyl | α | α |
| Compound 39 | β-Cl | 3 | cyclohexyl-methyl | hydrogen | α | α |
| Compound 40 | β-Cl | 3 | 2-methyl-1-hexyl | methyl | α | α |
| Compound 41 | β-Cl | 3 | 2-methyl-1-hexyl | hydrogen | α | α |
| Compound 42 | β-Cl | 3 | 2,6-dimethyl-5-heptenyl | methyl | α | α |
| Compound 43 | β-Cl | 3 | 2,6-dimethyl-5-heptenyl | hydrogen | α | α |
| Compound 44 | β-Cl | 3 | 1-methyl-3-hexynyl | methyl | α | α |
| Compound 45 | β-Cl | 3 | 1-methyl-3-hexynyl | hydrogen | α | α |

The compounds in the present invention can be administered orally or parenterally such as intravenously or nasally. For example, they can be administered orally in the form such as tablets, dusting powders, granules, powders, capsules, solutions, emulsions or suspensions, each of which can be prepared according to conventional methods. As the dosage forms for intravenous administration, there are used aqueous or non-aqueous solutions, emulsions, suspensions or solid preparations to be dissolved in a solvent for injection immediately before use. Furthermore, nasal administration can be performed by spraying quantitatively a solution or a powder (hard capsules) containing the drug into the nasal cavity by use of a dedicated nasal dropper or sprayer. Furthermore, the compounds in the present invention can be formulated into the form of inclusion compounds with α-, β- or γ-cyclodextrin, or methylated cyclodextrin. The dose is varied by the age, body weight, etc., but it generally is from 1 ng to 1 mg/day per adult.

INDUSTRIAL APPLICABILITY

The compounds of the present invention have a sufficient sleep-inducing action and an excellent stability, therefore they are useful as sleep-inducing agents.

BEST MODE FOR CARRYING OUT THE INVENTION

The present invention is illustrated in more detail by the following examples and experiments.

In the nomenclature of the compound, "nor" means the lack of a carbon atom at the position (e.g. 16,17,18,19,20-pentanor means the lack of carbon atoms from the 16- to 20-positions), and "homo" means the increase of a carbon atom (e.g. 1a-homo means the presence of a carbon atom at the 1a position between the 1- and 2-positions).

EXAMPLE 1

Preparation of 9-deoxy-9β-chloro-16,17,18,19,20-pentanor-15-cyclohexyl-2,2,3,3,13,14-hexadehydro-PGF$_1$α tert-butyl ester (Compound 8)

(1) Under an argon stream, (3S)-3-(tert-butyldimethyl-siloxy)-3-cyclohexylprop-1-yne (3.61 g) was dissolved in toluene (28.8 ml), and n-butyl lithium (1.95 M, hexane solution, 6.4 ml) was added at 0° C., followed by stirring at the same temperature for 30 minutes. To the solution was added diethylaluminium chloride (0.97 M, hexane solution, 14.8 ml) at 0° C., followed by stirring at room temperature for 30 minutes. To the solution was added (4R)-2-(N,N-diethylamino)methyl-4-(tert-butyldimethylsiloxy)cyclopent-2-en-1-one (0.25 M, toluene solution, 14.8 ml) at room temperature, followed by stirring for 15 minutes. The reaction solution was poured into a mixture of hexane (100 ml)—a saturated aqueous ammonium chloride solution (100 ml)—an aqueous hydrochloric acid solution (3N, 30 ml) with stirring, and the organic layer was separated and washed with a saturated aqueous sodium bicarbonate solution (50 ml). The resulting organic layer was dried over anhydrous magnesium sulfate, filtered and concentrated, and the resulting residue was purified by a silica gel column chromatography (developing solvent; hexane:ethyl acetate=10:1) to give (3R, 4R)-2-methylene-3-[(3S)-3-(tert-butyldimethylsiloxy)-3-cyclohexylprop-1'-ynyl]-4-(tert-butyldimethylsiloxy)cyclopentan-1-one (3.69 g).

$^1$H-NMR(CDCl$_3$, 200 MHz) δppm; 0.07, 0.08 and 0.12 (3s, 12H), 0.88(s, 18H), 0.92–1.92(m, 11H), 2.32(dd, J=17.8, 7.4 Hz, 1H), 2.71(dd, J=17.8, 6.5 Hz, 1H), 3.48–3.58 (m, 1H), 4.11(dd, J=6.2, 1.4 Hz, 1H), 4.20–4.32(m, 1H), 5.55(d, J=2.6 Hz, 1H), 6.13(d, J=3.0 Hz, 1H); IR(neat); 2930, 2850, 1375, 1640, 1470, 1380, 1255, 830, 770 cm$^{-1}$.

(2) Under an argon stream, copper (I) cyanide-dilithium dichloride (1.0 M, tetrahydrofuran solution, 41.21 ml) was added to 5-tert-butoxycarbonyl-4-pentynyl zinc (II) iodide (0.81 N, tetrahydrofuran solution, 40.69 ml) at −70° C., followed by stirring at the same temperature for 20 minutes. To the solution were added a diethyl ether solution (66.0 ml) of the compound (7.86 g) obtained in the above (1) and chlorotrimethylsilane (3.77 ml) at −70° C., and the temperature was raised to 0° C. with stirring over about an hour. The reaction solution, after addition of a saturated aqueous ammonium chloride solution (250 ml), was extracted with hexane. The organic layer was washed with a saturated aqueous sodium chloride solution, dried and concentrated, and the resulting residue was dissolved in diethyl ether (16.5 ml)—isopropyl alcohol (66.0 ml), and pyridinium p-toluenesulfonate (208 mg) was added, followed by stirring at room temperature for 12 hours. The reaction solution, after addition of hexane (200 ml), was washed with a saturated aqueous sodium bicarbonate solution and a saturated aqueous sodium chloride solution, dried and concentrated, and the resulting residue was purified by a silica gel column chromatography (developing solvent; hexane:ethyl acetate=15:1) to give 16,17,18,19,20-pentanor-15-cyclohexyl-2,2,3,3,13,14-hexadehydro-PGE$_1$ tert-butyl ester 11,15-bis(tert-butyldimethylsilyl)ether (5.73 g).

$^1$H-NMR(CDCl$_3$, 200 MHz) δppm; 0.08(s, 3H), 0.09(s, 3H), 0.10(s, 3H), 0.13(s, 3H), 0.89(s, 9H), 0.90(s, 9H), 0.96–1.96(m, 19H), 1.49(s, 9H), 1.97–2.35(m, 2H), 2.56–2.75(m, 2H), 4.03–4.19(m, 1H), 4.22–4.35(m, 1H); IR(neat); 2932, 2857, 2238, 1747, 1708, 1452, 1393, 1370, 1278, 1258, 1162, 1078, 840, 779, 755, 670 cm$^{-1}$.

(3) A methyl alcohol solution (94.7 ml) of the compound (5.73 g) obtained in the above (2) was cooled to 0° C., and potassium borohydride (1.02 g) was added, followed by stirring for 15 minutes. After addition of water, extraction was carried out with ether (200 ml), and the extract was washed with a saturated aqueous ammonium chloride solution and an aqueous sodium chloride solution, dried over anhydrous magnesium sulfate and concentrated. The residue was purified by a silica gel column chromatography (developing solvent; hexane:ethyl acetate=5:1) to give 16,17,18,19,20-pentanor-15-cyclohexyl-2,2,3,3,13,14-hexadehydro-PGF$_1$α tert-butyl ester 11,15-bis(tert-butyldimethylsilyl)ether (2.17 g) and 16,17,18,19,20-pentanor-15-cyclohexyl- 2,2,3,3,13,14-hexadehydro-PGF$_1$β tert-butyl ester 11,15-bis(tert-butyldimethylsilyl)ether (2.75 g).

16,17,18,19,20-pentanor-15-cyclohexyl-2,2,3,3,13,14-hexadehydro-PGF1α tert-butyl ester 11,15-bis(tert-butyldimethylsilyl)ether $^1$H-NMR(CDCl$_3$, 200 MHz) δppm; 0.09(s, 3H), 0.10(s, 3H), 0.11(s, 3H), 0.12(s, 3H), 0.90(s, 9H), 0.91(s, 9H), 0.94–2.07(m, 21H), 1.50(s, 9H), 2.26–2.38(m, 1H), 2.42–2.51(m,1H), 2.55(d, J=9.5 Hz, 1H), 4.02–4.20(m, 1H), 4.09(dd, J=6.4, 1.7 Hz, 1H), 4.24–4.33(m, 1H); IR(neat); 3468, 2930, 2856, 2236, 1709, 1473, 1463, 1392, 1370, 1277, 1257, 1162, 1104, 1075, 1006, 939, 899, 838, 778, 756, 668 cm$^{-1}$.

16,17,18,19,20-pentanor-15-cyclohexyl-2,2,3,3,13,14-hexadehydro-PGF$_1$β tert-butyl ester 11,15-bis(tert-butyldimethylsilyl)ether $^1$H-NMR(CDCl$_3$, 200 MHz) δppm; 0.07(s, 3H), 0.08(s, 6H), 0.11(s, 3H), 0.88(s, 9H), 0.90(s, 9H), 0.92–1.93(m, 21H), 1.49(s, 9H), 2.22(ddd, J=9.4,6.4, 1.7 Hz, 1H), 2.24–2.37(m, 1H), 3.91–4.28(m, 3H); IR(neat); 3435, 2930, 2857, 2237, 1710, 1473, 1463, 1392, 1370, 1277, 1257, 1162, 1073, 898, 838, 778, 756, 670 cm$^{-1}$.

(4) To a pyridine solution (4.95 ml) of 16,17,18,19,20-pentanor-15-cyclohexyl-2,2,3,3,13,14-hexadehydro-PGF$_1$α tert-butyl ester 11,15-bis(tert-butyldimethylsilyl)ether (641 mg) obtained in the above (3) was added methanesulfonyl chloride (0.153 ml) at 0° C., followed by stirring at room temperature for 2 hours. This was added to a toluene suspension (4.95 ml) of n-tetrabutylammonium chloride (4.40 g), followed by stirring at 40° C. overnight. After addition of a saturated aqueous sodium chloride solution (50 ml) and ethyl acetate (50 ml), the organic layer was separated, and the aqueous layer was extracted with ethyl acetate (20 ml). The resulting organic layers were combined, washed with a saturated aqueous sodium chloride solution, dried over anhydrous magnesium sulfate and filtered. The filtrate was concentrated under reduced pressure, and the resulting crude product was purified by a silica gel column chromatography (developing solvent; hexane:ethyl acetate=25:1–10:1) to give 9-deoxy-9β-chloro-16,17,18,19,20-pentanor-15-cyclohexyl-2,2,3,3,13,14-hexadehydro-PGF$_1$α tert-butyl ester 11,15-bis(tert-butyldimethylsilyl)ether (624 mg).

$^1$H-NMR(CDCl$_3$, 200 MHz) δppm; 0.07(s, 3H), 0.08(s, 6H), 0.11(s, 3H), 0.88(s, 9H), 0.90(s, 9H), 0.93–1.92(m, 19H), 1.49(s, 9H), 1.94–2.19(m, 1H), 2.14(dd, J=7.8, 5.4 Hz, 1H), 2.23–2.37(m, 2H), 3.87–4.03(m, 1H), 4.08(dd, J=6.2, 1.7 Hz, 1H), 4.18–4.29(m, 1H); IR(neat); 2930, 2856, 2237, 1709, 1473, 1463, 1392, 1369, 1276, 1257, 1163, 1102, 1077, 1006, 899, 838, 778, 755, 670 cm$^{-1}$.

(5) To an acetonitrile solution (30.2 ml) of the compound (604 mg) obtained in the above (4) was added an aqueous hydrofluoric acid solution (46%, 8.80 ml) at 0° C., followed by stirring at the same temperature for 2 hours. The reaction solution was poured into a mixture of ethyl acetate (100 ml) and a saturated aqueous sodium bicarbonate solution (155 ml) with stirring, the organic layer was separated, and the aqueous layer was extracted with ethyl acetate (20 ml). The resulting organic layers were combined, washed with a saturated aqueous sodium chloride solution, dried over anhydrous magnesium sulfate and filtered. The filtrate was concentrated under reduced pressure, and the resulting crude product was purified by a silica gel column chromatography (developing solvent; hexane:ethyl acetate=1:1) to give the title compound (295 mg).

$^1$H-NMR(CDCl$_3$, 300 MHz) δppm; 0.95–1.34(m, 6H), 1.45–1.89(m, 11H), 1.49(s, 9H), 2.03–2.38(m, 8H), 3.89–4.00(m, 1H), 4.16(dd, J=6.1, 1.9 Hz, 1H), 4.32–4.41 (m, 1H); IR(neat); 3391, 2980, 2930, 2855, 2237, 1707, 1478, 1452, 1395, 1370, 1278, 1161, 1081, 1032, 894, 845, 756, 692 cm$^{-1}$.

EXAMPLE 2

Preparation of 9-deoxy-9β-chloro-16,17,18,19,20-pentanor-15-cyclohexyl-2,2,3,3,13,14-hexadehydro-PGF$_1$α methyl ester (Compound 13)

(1) Following the same manner as in Example 1(2) using 5-carbomethoxy-4-pentynyl zinc (II) iodide in place of 5-tert-butoxycarbonyl-4-pentynyl zinc (II) iodide, thereby 16,17,18,19,20-pentanor-15-cyclohexyl-2,2,3,3,13,14-hexadehydro-PGE$_1$ methyl ester 11,15-bis(tert-butyldimethylsilyl)ether was obtained.

$^1$H-NMR(CDCl$_3$, 200 MHz) δppm; 0.07(s, 3H), 0.09(s, 3H), 0.10(s, 3H), 0.12(s, 3H), 0.82–1.92(m, 17H), 0.89(s, 9H), 0.90(s, 9H), 2.14–2.28(m, 1H), 2.17(dd, J=18.3, 7.1 Hz, 1H), 2.28–2.40(m, 2H), 2.68(ddd, J=18.3, 6.8, 1.3 Hz, 1H), 2.69(ddd, J=9.5, 6.8, 1.6 Hz, 1H), 3.75(s, 3H), 4.09(dd, J=6.2, 1.6 Hz, 1H), 4.29(q, J=6.8 Hz, 1H); IR(neat); 2930, 2857, 2236, 1748, 1718, 1472, 1463, 1452, 1435, 1407, 1374, 1362, 1337, 1256, 1102, 1078, 1007, 940, 898, 839, 779, 753, 670 cm$^{-1}$.

(2) Following the same manner as in Example 1(3) using the compound obtained in the above (1), 16,17,18,19,20-pentanor-15-cyclohexyl-2,2,3,3,13,14-hexadehydro- PGF$_1\alpha$ methyl ester 11,15-bis(tert-butyldimethylsilyl) ether and 16,17,18,19,20-pentanor-15-cyclohexyl-2,2,3,3,13,14-hexadehydro-PGF$_1\beta$ methyl ester 11,15-bis(tert-butyldimethylsilyl)ether were obtained.

16,17,18,19,20-pentanor-15-cyclohexyl-2,2,3,3,13,14-hexadehydro-PGF$_1\alpha$ methyl ester 11,15-bis(tert-butyldimethylsilyl)ether $^1$H-NMR(CDCl$_3$, 200 MHz) δppm; 0.08(s, 3H), 0.09(s, 3H), 0.10(s, 3H), 0.11(s, 3H), 0.82–2.07(m, 20H), 0.88(s, 9H), 0.90(s, 9H), 2.35–2.50(m, 1H), 2.35(t, J=6.7 Hz, 2H), 3.75(s, 3H), 4.02–4.17(m, 1H), 4.07(dd, J=6.2, 1.9 Hz, 1H), 4.24–4.32(m, 1H); IR(neat); 3468, 2930, 2856, 2238, 1719, 1472, 1463, 1435, 1386, 1362, 1337, 1255, 1104, 1077, 1006, 963, 927, 898, 838, 778, 754, 668 cm$^{-1}$.

16,17,18,19,20-pentanor-15-cyclohexyl-2,2,3,3,13,14-hexadehydro-PGF$_1\beta$ methyl ester 11,15-bis(tert-butyldimethylsilyl)ether $^1$H-NMR(CDCl$_3$, 200 MHz) δppm; 0.07(s, 3H), 0.08(s, 6H), 0.11(s, 3H), 0.82–1.95(m, 20H), 0.88(s, 9H), 0.90(s, 9H), 2.25(ddd, J=9.3, 6.2, 1.6 Hz, 1H), 2.35(t, J=6.6 Hz, 2H), 3.75(s, 3H), 3.91–4.04(m, 1H), 4.08(dd, J=6.2, 1.6 Hz, 1H), 4.15–4.30(m, 1H); IR(neat); 3441, 2929, 2856, 2239, 1719, 1472, 1463, 1436, 1388, 1361, 1337, 1103, 1074, 1006, 962, 899, 838, 778, 754, 670 cm$^{-1}$.

(3) Following the same manner as in Example 1(4) using 16,17,18,19,20-pentanor-15-cyclohexyl-2,2,3,3,13,14-hexadehydro-PGF$_1\alpha$ methyl ester 11,15-bis(tert-butyldimethylsilyl)ether obtained in the above (2), thereby 9-deoxy-9β-chloro-16,17,18,19,20-pentanor-15-cyclohexyl-2,2,3,3,13,14-hexadehydro-PGF$_1\alpha$ methyl ester 11,15-bis(tert-butyldimethylsilyl)ether was obtained.

$^1$H-NMR(CDCl$_3$, 200 MHz) δppm; 0.07(s, 3H), 0.08(s, 6H), 0.11(s, 3H), 0.50–1.92(m, 17H), 0.88(s, 9H), 0.90(s, 9H), 1.95–2.20(m, 1H), 2.14(dd, J=7.7, 5.5 Hz, 1H), 2.23–2.42(m, 4H), 3.76(s, 3H), 3.95(q, J=7.7 Hz, 1H), 4.08(dd, J=6.2, 1.7 Hz, 1H), 4.25–4.30(m, 1H); IR(neat); 2930, 2856, 2239, 1719, 1472, 1463, 1435, 1362, 1338, 1255, 1102, 1078, 1006, 963, 899, 838, 778, 753, 670 cm$^{-1}$.

(4) Following the same manner as in Example 1(5) using the compound obtained in the above (3), thereby the title compound was obtained.

$^1$H-NMR(CDCl$_3$, 300 MHz) δppm; 0.96–1.35(m, 6H), 1.47–1.91(m, 11H), 2.09–2.41(m, 6H), 3.76(s, 3H), 3.95(q, J=7.4 Hz, 1H), 4.16(dd, J=6.1, 1.9 Hz, 1H), 4.37(q, J=6.3 Hz, 1H); IR(neat); 3392, 2928, 2855, 2238, 1715, 1436, 1384, 1260, 1156, 1080, 1012, 955, 894, 822, 754, 692 cm$^{-1}$.

EXAMPLE 3

Preparation of 9-deoxy-9p-chloro-16,17,18,19,20-pentanor-15-cyclohexyl-2,2,3,3,13,14-hexadehydro-PGF$_1\alpha$ (Compound 14)

An acetone solution (22.4 ml) of the compound (410 mg) obtained in Example 2 was added to a suspension of lipase PS (11.7 g) in water (66 ml), and phosphate buffer (pH 7.0) (11.3 ml) and water (161 ml) were added, followed by stirring at 38° C. for 12 hours. The reaction solution, after filtration, was extracted with ethyl acetate. The organic layer was washed with a saturated aqueous sodium chloride solution, dried over anhydrous magnesium sulfate and then filtered. The filtrate was concentrated under reduced pressure, and the resulting crude product was purified by a silica gel column chromatography (developing solvent; ethyl acetate) to give the title compound (400 mg).

$^1$H-NMR(CDCl$_3$, 300 MHz) δppm; 0.76–2.44(m, 14H), 2.34(ddd, J=9.5, 6.2, 1.9 Hz, 1H), 2.41(t, J=6.3 Hz, 1H), 3.89–3.99(m, 1H), 4.18(dd, J=6.1, 1.9 Hz, 1H), 4.32–4.41(m, 1H); IR(neat); 3368, 2928, 2854, 2237, 1694, 1451, 1385, 1262, 1082, 1007, 893, 758, 595 cm$^{-1}$.

EXAMPLE 4

Preparation of 9-deoxy-9β-chloro-17,18,19,20-tetranor-16-cyclopentyl-2,2,3,3,13,14-hexadehydro-PGF$_1\alpha$ methyl ester (Compound 32)

(1) Following the same manner as in Example 1(2) using 5-carbomethoxy-4-pentynyl zinc (II) iodide and (3R, 4R)-2-methylene-3-[(3S)-3-(tert-butyldimethylsiloxy)-4-cyclopentylbutan-1-ynyl]-4-(tert-butyldimethyl-siloxy)cyclopentan-1-one, respectively, in place of 5-tert-butoxycarbonyl-4-pentynyl zinc (II) iodide and (3R, 4R)-2-methylene-3-[(3S)-3-(tert-butyldimethylsiloxy)-3-cyclohexylprop-1-ynyl]-4-(tert-butyldimethyl-siloxy)cyclopentan-1-one, thereby 17,18,19,20-tetranor-16-cyclopentyl-2,2,3,3,13,14-hexadehydro-PGE$_1$ methyl ester 11,15-bis(tert-butyldimethylsilyl)ether was obtained.

$^1$H-NMR(CDCl$_3$, 200 MHz) δppm; 0.10(s, 6H), 0.11(s, 3H), 0.13(s, 3H), 0.89(s, 9H), 0.90(s, 9H), 0.96–2.40(m, 20H), 2.17(dd, J=18.2, 7.0 Hz, 1H), 2.60–2.76(m, 2H), 3.76(s, 3H), 4.22–4.43(m, 1H), 4.37(dt, J=1.7, 6.8 Hz, 1H); IR(neat); 2952, 2930, 2858, 2237, 1749, 1718, 1472, 1463, 1435, 1361, 1256, 1078, 1005, 939, 838, 778, 753, 670, 562 cm$^{-1}$.

(2) Following the same manner as in Example 1(3) using the compound obtained in the above (1), thereby 17,18,19,20-tetranor-16-cyclopentyl-2,2,3,3,13,14-hexadehydro-PGF$_1\alpha$ methyl ester 11,15-bis(tert-butyldimethylsilyl) ether and 17,18,19,20-tetranor-16-cyclopentyl-2,2,3,3,13,14-hexadehydro-PGF$_1\beta$ methyl ester 11,15-bis(tert-butyldimethylsilyl)ether were obtained.

17,18,19,20-tetranor-16-cyclopentyl-2,2,3,3,13,14-hexadehydro-PGF$_1\alpha$ methyl ester 11,15-bis(tert-butyldimethylsilyl)ether $^1$H-NMR(CDCl$_3$, 200 MHz) δppm; 0.09(s, 3H), 0.10(s, 6H), 0.11(s, 3H), 0.88(s, 9H), 0.90(s, 9H), 1.38–2.06(m, 20H), 2.29–2.49(m, 1H), 2.36(t, J=6.7 Hz, 2H), 2.53(d, J=9.4 Hz, 1H), 3.76(s, 3H), 4.05–4.18(m, 1H), 4.23–4.40(m, 1H), 4.35(dt, J=1.9, 7.0 Hz, 1H); IR(neat); 3467, 2951, 2930, 2857, 2237, 1718, 1472, 1463, 1435, 1388, 1361, 1336, 1255, 1077, 1005, 939, 869, 837, 777, 753, 667 cm$^{-1}$.

17,18,19,20-tetranor-16-cyclopentyl-2,2,3,3,13,14-hexadehydro-PGF$_1\beta$ methyl ester 11,15-bis(tert-butyldimethylsilyl)ether $^1$H-NMR(CDCl$_3$, 200 MHz) δppm; 0.07(s, 3H), 0.09(s, 3H), 0.10(s, 3H), 0.12(s, 3H), 0.88(s, 9H), 0.90(s, 9H), 0.98–2.07(m, 21H), 2.22(ddd, J=9.2, 6.3, 1.7 Hz, 1H), 2.35(t, J=6.8 Hz, 2H), 3.76(s, 3H), 3.90–4.06(m, 1H), 4.16–4.29(m, 1H), 4.36(dt, J=1.6, 6.8 Hz, 1H); IR(neat); 3435, 2951, 2930, 2857, 2237, 1718, 1472, 1463, 1435, 1387, 1361, 1335, 1255, 1075, 1005, 939, 836, 777, 753, 669 cm$^{-1}$.

(3) Following the same manner as in Example 1(4) using 17,18,19,20-tetranor-16-cyclopentyl-2,2,3,3,13,14-hexadehydro-PGF$_1\alpha$ methyl ester 11,15-bis(tert-butyldimethylsilyl)ether obtained in the above (2), thereby 9-deoxy-9β-chloro-17,18,19,20-tetranor-16-cyclopentyl-2,2,3,3,13,14-hexadehydro-PGF$_1$α methyl ester 11,15-bis(tert-butyldimethylsilyl)ether was obtained.

$^1$H-NMR(CDCl$_3$, 200 MHz) δppm; 0.07(s, 3H), 0.08(s, 3H), 0.10(s, 3H), 0.12(s, 3H), 0.88(s, 9H), 0.90(s, 9H), 1.00–2.41 (m, 23H), 3.76(s, 3H), 3.87–4.03(m, 1H), 4.19–4.30(m, 1H), 4.35(dt, J=1.6, 6.8 Hz, 1H); IR(neat); 2951, 2930, 2857, 2238, 1718, 1472, 1463, 1434, 1387, 1361, 1252, 1077, 1005, 939, 904, 836, 777, 752, 669 cm$^{-1}$.

(4) Following the same manner as in Example 1(5) using the compound obtained in the above (3), thereby the title compound was obtained.

$^1$H-NMR(CDCl$_3$, 200 MHz) δppm; 1.02–1.31(m, 4H), 1.44–2.46(m, 19H), 1.92(d, J=5.9 Hz, 1H), 2.04(d, J=4.4 Hz, 1H), 3.77(s, 3H), 3.88–4.03(m, 1H), 4.29–4.46(m, 2H); IR(neat); 3368, 2945, 2863, 2236, 1715, 1435, 1257, 1161, 1078, 1045, 820, 753cm$^{-1}$.

EXAMPLE 5

Preparation of 9-deoxy-9β-chloro-17,18,19,20-tetranor-16-cyclopentyl-2,2,3,3,13,14-hexadehydro-PGF$_1$α (Compound 33)

Following the substantially same manner as in Example 3 using the compound obtained in Example 4, thereby the title compound was obtained.

$^1$H-NMR(CDCl$_3$, 200 MHz) δppm; 1.03–2.48(m, 23H), 2.74–3.20(br, 3H), 3.87–4.03(m, 1H), 4.29–4.47(m, 2H); IR(neat); 3367, 2944, 2863, 2623, 2236, 1695, 1450, 1262, 1167, 1077, 1042, 990, 872, 757, 594 cm$^{-1}$.

EXAMPLE 6

Preparation of 9-deoxy-9β-chloro-17,18,19,20-tetranor-16-cyclohexyl-2,2,3,3,13,14-hexadehydro-PGF$_1$α methyl ester (Compound 38)

(1) Following the same manner as in Example 1(2) using 5-carbomethoxy-4-pentynyl zinc (II) iodide and (3R, 4R)-2-methylene-3-[(3S)-3-(tert-butyldimethylsiloxy)-4-cyclohexylbutan-1-ynyl]-4-(tert-butyldimethyl-siloxy) cyclopentan-1-one, respectively, in place of 5-tert-butoxycarbonyl-4-pentynyl zinc (II) iodide and (3R, 4R)-2-methylene-3-[(3S)-3-(tert-butyldimethylsiloxy)-3-cyclohexylprop-1-ynyl]-4-(tert-butyldimethyl-siloxy) cyclopentan-1-one, thereby 17,18,19,20-tetranor-16-cyclohexyl-2,2,3,3,13,14-hexadehydro-PGE$_1$ methyl ester 11,15-bis(tert-butyldimethylsilyl)ether was obtained.

$^1$H-NMR(CDCl$_3$, 200 MHz) δppm; 0.10(s, 6H), 0.11(s, 3H), 0.13(s, 3H), 0.90(s, 18H), 1.10–1.80(m, 19H), 2.14–2.27(m, 1H), 2.17(dd, J=18.2, 7.0 Hz, 1H), 2.34(t, J=6.6 Hz,2H), 2.60–2.75(m, 2H), 3.76(s, 3H), 4.23–4.35(m, 1H), 4.45(dt, J=1.4 Hz, 7.9 Hz,1H); IR(neat); 2928, 2856, 2238, 1748, 1718, 1472, 1463, 1435, 1362, 1256, 1077 cm$^{-1}$.

(2) Following the same manner as in Example 1(3) using the compound obtained in the above (1), thereby 17,18,19,20-tetranor-16-cyclohexyl-2,2,3,3,13,14-hexadehydro-PGF$_1$α methyl ester 11,15-bis(tert-butyldimethylsilyl) ether and 17,18,19,20-tetranor-16-cyclohexyl-2,2,3,3,13,14-hexadehydro-PGF$_1$β methyl ester 11,15-bis(tert-butyldimethylsilyl)ether were obtained.

17,18,19,20-tetranor-16-cyclohexyl-2,2,3,3,13,14-hexadehydro-PGF$_1$α methyl ester 11,15-bis(tert-butyldimethylsilyl)ether $^1$H-NMR(CDCl$_3$, 200 MHz) δppm; 0.09(s, 6H), 0.11(s, 6H), 0.78–2.06(m, 22H), 0.88(s, 9H), 0.90(s, 9H), 2.29–2.49 (m, 1H), 2.36(t, J=6.7 Hz, 2H), 2.54(d, J=9.7 Hz, 1H), 3.76(s, 3H), 4.06–4.20(m, 1H), 4.22–4.33(m, 1H), 4.37–4.49(m, 1H); IR(neat); 3435, 2928, 2855, 2237, 1718, 1472, 1463, 1448, 1435, 1388, 1361, 1252, 1074, 1003, 938, 837, 777, 753, 667 cm$^{-1}$.

17,18,19,20-tetranor-16-cyclohexyl-2,2,3,3,13,14-hexadehydro-PGF$_1$β methyl ester 11,15-bis(tert-butyldimethylsilyl)ether $^1$H-NMR(CDCl$_3$, 200 MHz) δppm; 0.08(s, 3H), 0.09(s, 3H), 0.10(s, 3H), 0.11(s, 3H), 0.77–1.94(m, 23H), 0.88(s, 9H), 0.90(s, 9H), 2.22(ddd, J=9.3, 6.3, 1.9 Hz, 1H), 2.35(t, J=6.9 Hz,2H), 3.76(s, 3H), 3.91–4.06(m, 1H), 4.16–4.29(m, 1H), 4.38–4.49(m, 1H); IR(neat); 3436, 2928, 2855, 2237, 1718, 1472, 1463, 1448, 1435, 1388, 1361, 1255, 1074, 1004, 938, 889, 836, 777, 753, 669, 568 cm$^{-1}$.

(3) Following the same manner as in Example 1(4) using 17,18,19,20-tetranor-16-cyclohexyl-2,2,3,3,13,14-hexadehydro-PGF$_1$α methyl ester 11,15-bis(tert-butyldimethylsilyl)ether obtained in the above (2), thereby 9-deoxy-9β-chloro-17,18,19,20-tetranor-16-cyclohexyl-2,2,3,3,13,14-hexadehydro-PGF$_1$α methyl ester 11,15-bis(tert-butyldimethylsilyl)ether was obtained.

$^1$H-NMR(CDCl$_3$, 200 MHz) δppm; 0.07(s, 3H), 0.09(s, 3H), 0.10(s, 3H), 0.11(s, 3H), 0.78–1.78(m, 19H), 0.88(s, 9H), 0.90(s, 9H), 1.99–2.41(m, 6H), 3.76(s, 3H), 3.87–4.03 (m, 1H), 4.19–4.30(m, 1H), 4.37–4.49(m, 1H); IR(neat); 2928, 2855, 2238, 1719, 1472, 1463, 1448, 1434, 1388, 1361, 1252, 1075, 1004, 938, 909, 891, 836, 777, 752, 668 cm$^{-1}$.

(4) Following the same manner as in Example 1(5) using the compound obtained in the above (3), thereby the title compound was obtained.

$^1$H-NMR(CDCl$_3$, 200 MHz) δppm; 0.82–1.84(m, 19H), 1.90(d, J=5.9 Hz, 1H), 2.00–2.44(m, 6H), 2.04(d, J=3.5 Hz, 1H), 3.77(s, 3H), 3.88–4.03(m, 1H), 4.29–4.54(m, 2H); IR(neat); 3400, 2924, 2851, 2237, 1716, 1435, 1256, 1156, 1078, 1044, 981, 821, 753 cm$^{-1}$.

EXAMPLE 7

Preparation of 9-deoxy-9β-chloro-17,18,19,20-tetranor-16-cyclohexyl-2,2,3,3,13,14-hexadehydro-PGF$_1$α (Compound 39)

Following the substantially same manner as in Example 3 using the compound obtained in Example 6, thereby the title compound was obtained.

$^1$H-NMR(CDCl$_3$, 200 MHz) δppm; 0.82–1.84(m, 19H), 2.02–2.72(m, 9H), 3.88–4.02(m, 1H), 4.29–4.54(m, 2H); IR(neat); 3350, 2924, 2852, 2625, 2236, 1691, 1448, 1267, 1061, 1042, 980, 894, 757, 594 cm$^{-1}$.

EXAMPLE 8

Preparation of 9-deoxy-9β-chloro-1a-homo-16,17,18,19,20-pentanor-15-cyclohexyl-1a,1a,2,2,13,14-hexadehydro-PGF$_1$α methyl ester (Compound 19)

(1) Following the same manner as in Example 1(2) using 6-carbomethoxy-5-hexynyl zinc (II) iodide in place of 5-tert-butoxycarbonyl-4-pentynyl zinc (II) iodide, thereby 1a-homo-16,17,18,19,20-pentanor-15-cyclohexyl-1a,1a,2,2,13,14-hexahydro-PGE$_1$ methyl ester 11,15-bis(tert-butyldimethylsilyl)ether was obtained.

$^1$H-NMR(CDCl$_3$, 200 MHz) δppm; 0.08(s, 3H), 0.09(s, 3H), 0.10(s, 3H), 0.13(s, 3H), 0.78–1.94(m, 19H), 0.89(s, 9H), 0.90(s, 9H), 2.09–2.27(m, 1H), 2.17(dd, J=18.2, 7.1 Hz, 1H), 2.33(t, J=6.9 Hz, 2H), 2.59–2.76(m, 1H), 2.68(ddd, J=18.2, 6.7, 1.2 Hz, 1H), 3.76(s, 3H), 4.09(dd, J=6.2, 1.5 Hz, 1H), 4.22–4.36(m, 1H); IR(neat); 2929, 2856, 2238, 1748, 1718, 1472, 1463, 1451, 1435, 1406, 1374, 1361, 1337, 1255, 1100, 1077, 1006, 939, 898, 881, 837, 778, 753, 669, 587 cm$^{-1}$.

(2) Following the same manner as in Example 1(3) using the compound obtained in the above (1), thereby 1a-homo-16,17,18,19,20-pentanor-15-cyclohexyl-1a,1a,2,2,13,14-hexahydro-PGF$_1$α methyl ester 11,15-bis(tert-butyldimethylsilyl)ether and 1a-homo-16,17,18,19,20-pentanor-15-cyclohexyl-1a,1a,2,2,13,14-hexahydro-PGF$_1$β methyl ester 11,15-bis(tert-butyldimethylsilyl)ether were obtained.

1a-homo-16,17,18,19,20-pentanor-15-cyclohexyl-1a,1a,2,2,13,14-hexahydro-PGF$_1$α methyl ester 11,15-bis(tert-butyldimethylsilyl)ether $^1$H-NMR(CDCl$_3$, 200 MHz) δppm; 0.08(s, 3H), 0.09(s, 3H), 0.10(s, 3H), 0.11(s, 3H), 0.82–2.06(m, 22H), 0.89(s, 9H), 0.90(s, 9H), 2.34(t, J=7.0 Hz, 2H), 2.40–2.52(m, 1H), 2.53(d, J=9.7 Hz, 1H), 3.76(s, 3H), 4.02–4.18(m, 1H), 4.07(dd, J=6.3, 1.9 Hz, 1H), 4.22–4.35(m, 1H); IR(neat); 3436, 2929, 2855, 2238, 1718, 1472, 1463, 1451, 1435, 1386, 1361, 1336, 1255, 1103, 1074, 1005, 963, 939, 898, 836, 777, 753, 668 cm$^{-1}$.

1a-homo-16,17,18,19, 20-pentanor-15-cyclohexyl-1a,1a,2,2,13,14-hexahydro-PGF$_1$β methyl ester 11,15-bis (tert-butyldimethylsilyl)ether $^1$H-NMR(CDCl$_3$, 200 MHz) δppm; 0.07(s, 3H), 0.08(s, 6H), 0.11(s, 3H), 0.76–1.94(m, 20H), 0.88(s, 9H), 0.90(s, 9H), 1.52(d, J=5.1 Hz, 1H), 1.88(t, J=6.4 Hz, 2H), 2.23(ddd, J=9.3, 6.3, 1.6 Hz, 1H), 2.34(t, J=6.9 Hz, 2H), 3.76(s, 3H), 3.90–4.04(m, 1H), 4.08(dd, J=6.3, 1.6 Hz, 1H), 4.16–4.30 (m, 1H); IR(neat); 3426, 2929, 2855, 2238, 1718, 1472, 1463, 1451, 1435, 1388, 1361, 1337, 1255, 1188, 1073, 1006, 962, 938, 927, 898, 836, 777, 753, 669, 583 cm$^{-1}$.

(3) Following the same manner as in Example 1(4) using 1a-homo-16,17,18,19, 20-pentanor-15-cyclohexyl-1a,1a,2,2,13,14-hexahydro-PGF$_1$α methyl ester 11,15-bis (tert-butyldimethylsilyl)ether obtained in the above (2), thereby 9-deoxy-9β-chloro-1a-homo-16,17,18,19,20-pentanor-15-cyclohexyl-1a,1a,2,2,13,14-hexahydro-PGF$_1$α methyl ester 11, 15-bis(tert-butyldimethylsilyl) ether was obtained.

$^1$H-NMR(CDCl$_3$, 200 MHz) δppm; 0.07(s, 3H), 0.08(2s, 6H), 0.11(s, 3H), 0.82–1.91(m, 19H), 0.88(s, 9H), 0.90(s, 9H), 1.96–2.19(m, 1H), 2.14(dd, J=7.6, 5.6 Hz, 2H), 2.28 (ddd, J=8.9, 5.1, 1.6 Hz, 1H), 2.34(t, J=6.9 Hz, 2H), 3.76(s, 3H), 3.88–4.02(m, 1H), 4.08(dd, J=6.2, 1.6 Hz, 1H), 4.20–4.30(m, 1H); IR(neat); 2929, 2855, 2238, 1718, 1472, 1463, 1451, 1435, 1388, 1361, 1337, 1255, 1188, 1100, 1077, 1006, 962, 939, 927, 898, 836, 814, 777, 752, 669, 587 cm$^{-1}$.

(4) Following the same manner as in Example 1(5) using the compound obtained in the above (3), thereby the title compound was obtained.

$^1$H-NMR(CDCl$_3$, 300 MHz) δppm; 0.84–1.90(m, 19H), 1.85(d, J=5.8 Hz, 1H), 2.06–2.39(m, 4H), 2.18(d, J=3.6 Hz, 1H), 2.35(t, J=6.9 Hz, 2H), 3.76(s, 3H), 3.90–4.00(m, 1H), 4.17(dt, J=1.8, 5.8 Hz, 1H), 4.32–4.42(m, 1H); IR(neat); 3368, 2928, 2854, 2237, 1715, 1435, 1256, 1156, 1079, 1011, 893, 847, 805, 753 cm$^{-1}$.

EXAMPLE 9

Preparation of 9-deoxy-9β-chloro-1a-homo-16,17,18,19,20-pentanor-15-cyclohexyl-1a,1a,2,2,13,14-hexahydro-PGF$_1$α (Compound 20)

Following the substantially same manner as in Example 3 using the compound obtained in Example 8, thereby the title compound was obtained.

$^1$H-NMR(CDCl$_3$, 300 MHz) δppm; 0.85–1.89(m, 19H), 2.09–2.42(m, 4H), 2.38(t, J=6.9 Hz, 2H), 2.70–3.40(br, 3H), 3.91–4.00(m, 1H), 4.19(dd, J=6.1, 1.9 Hz, 1H), 4.32–4.42 (m, 1H); IR(neat); 3368, 2929, 2854, 2624, 2236, 1691, 1450, 1262, 1081, 1006, 893, 757, 595 cm$^{-1}$.

Experiment [Sleep-inducing test by cisternal administration]

Method:

Four male crab-eating monkeys weighing 2.0–3.5 kg were individually placed in cages, and the behaviors of the animals were recorded by videotape for an hour before administration of the drug and for 3 hours after administration of the drug. Compound 14 was dissolved in saline solution and sterilized through a Millipore filter. The drug was infused cisternally into the monkeys anesthetized with isoflurane inhalation. The doses were 1 μg and 10 μg/0.1 ml/monkey. The same doses of the vehicle were infused cisternally to give a control group. The test was carried out according to the following test schedule.

Week 1: Group treated with vehicle

Week 2: Group treated with 1 μg of Compound 14/monkey

Week 3: Group treated with 10 μg of Compound 14/monkey

To determine the sleep, the time for which the monkey was relaxed closing both eyes was measured by playing back the recorded videotape. The sleep time (sec.) per hour was determined and is shown in Table 2.

TABLE 2

| | Sleep time (sec.) | | | Number of |
|---|---|---|---|---|
| | 0 - 1h | 1 - 2h | 2 - 3h | slept monkeys |
| Vehicle-treated Group | 0 | 0 | 0 | 0/4 |
| 1 μg/monkey | 739 | 1091 | 735 | 3/4 |
| 10 μg/monkey | 817 | 2088 | 1825 | 4/4 |

What is claimed is:

1. A prostaglandin derivative represented by Formula (I):

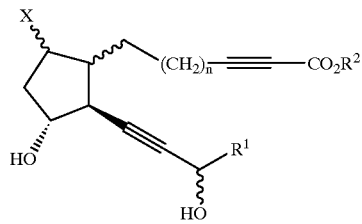

(I)

wherein X is a halogen atom, n is an integer of 1 to 5, $R^1$ is a $C_{3-10}$ cycloalkyl group, a $C_{3-10}$ cycloalkyl group substituted with $C_{1-4}$ alkyl group(s), a $C_{4-13}$ cycloalkylalkyl group, a $C_{5-10}$ alkyl group, a $C_{5-10}$ alkenyl group, a $C_{5-10}$ alkynyl group or a bridged cyclic hydrocarbon group, and $R^2$ is a hydrogen atom, a $C_{1-10}$ alkyl group or a $C_{3-10}$ cycloalkyl group, or a pharmaceutically acceptable salt thereof.

2. A prostaglandin derivative represented by Formula (I) according to claim 1 wherein $R^1$ is a $C_{3-10}$ cycloalkyl group, a $C_{3-10}$ cycloalkyl group substituted with $C_{1-4}$ alkyl group(s) or a $C_{4-13}$ cycloalkylalkyl group, or a pharmaceutically acceptable salt thereof.

3. A pharmaceutical composition which comprises as an effective ingredient the prostaglandin derivative according to claim 1 or 2, or the pharmaceutically acceptable salt thereof.

4. The prostaglandin derivative or the pharmaceutically acceptable salt thereof according to claim 1 or 2, for use as a pharmaceutically effective ingredient.

5. A sleep-inducing preparation which comprises as an effective ingredient the prostaglandin derivative or the pharmaceutically acceptable salt thereof according to claim 1 or 2.

6. A method for sleep-inducing comprising administering a pharmacologically effective amount of the prostaglandin derivative or the pharmaceutically acceptable salt according to claim 1 or 2 to a human.

* * * * *